United States Patent
Trevino (10) Patent No.: US 9,424,495 B1
(45) Date of Patent: Aug. 23, 2016

(54) DIGITAL FOOD IMAGING ANALYSIS: SYSTEM AND METHOD TO ANALYZE FOOD CONSUMPTION

(71) Applicant: Social & Health Research Center, San Antonio, TX (US)

(72) Inventor: Roberto Trevino, San Antonio, TX (US)

(*) Notice: Subject to any disclaimer, the term of this patent is extended or adjusted under 35 U.S.C. 154(b) by 0 days.

(21) Appl. No.: 14/687,917

(22) Filed: Apr. 16, 2015

(51) Int. Cl.
- *G06K 9/00* (2006.01)
- *G06K 9/78* (2006.01)
- *G06K 9/62* (2006.01)
- *G06T 7/40* (2006.01)
- *A61B 5/00* (2006.01)

(52) U.S. Cl.
CPC ............... *G06K 9/78* (2013.01); *A61B 5/486* (2013.01); *A61B 5/4866* (2013.01); *G06K 9/6267* (2013.01); *G06T 7/408* (2013.01); *G06T 2207/30128* (2013.01)

(58) Field of Classification Search
None
See application file for complete search history.

(56) References Cited

U.S. PATENT DOCUMENTS

| | | | |
|---|---|---|---|
| 8,363,913 B2 | 1/2013 | Boushey | |
| 8,439,683 B2 | 5/2013 | Puri | |
| 2003/0076983 A1 | 4/2003 | Cox | |
| 2008/0077493 A1* | 3/2008 | Geffert | G06Q 20/202 705/21 |
| 2009/0271243 A1* | 10/2009 | Sholl | G06Q 30/018 434/365 |
| 2013/0335418 A1* | 12/2013 | Kim | G06Q 10/00 345/424 |
| 2014/0104385 A1* | 4/2014 | Wong | G06Q 10/10 348/46 |
| 2016/0035248 A1* | 2/2016 | Gibbs | G06T 7/0002 434/127 |
| 2016/0063734 A1* | 3/2016 | Divakaran | G06T 7/0004 382/110 |
| 2016/0091419 A1* | 3/2016 | Watson | G01N 21/31 356/407 |

FOREIGN PATENT DOCUMENTS

KR  WO 2012115297 A1 * 8/2012 ............. G06Q 10/00

OTHER PUBLICATIONS

Roberto P. Trevino, T.H. Pham, and S.L Edelstein, Obesity and Preference-Weighted Quality of Life of Ethnically Diverse Middle School Children: The Healthy Study. Journal of Obesity, vol. 2013, USA.

Ofei, E. The Dietary Intake Monitoring System (DIMS)—an Innovative Device for Capturing Patient's Food Choice, Food Intake and Plate Waste in a Hospital Setting. Proceedings of Measuring Behavior 2014. NL.

Chae, J. Volume Estimation Using Food Specific Shape Templates in Mobile Image-Based Dietary Assessment. Proc SPIE. Author manuscript; available in PMC Oct. 22, 2011. US.

Nelson, M., and Darbyshire, S. Food photography II: use of food photographs for estimating portion size and the nutrient content of meals. The British Journal of Nutrition [Br J Nutr] Jul. 1996; vol. 76 (1), pp. 31-49. U.K.

Lazarte, C. Validation of digital photographs, as a tool in 24-h recall, for the improvement of dietary assessment among rural populations in developing countries. Nutrition Journal [Nutr J] Aug. 29, 2012; vol. 11, pp. 61. Date of Electronic Publication: Aug. 29, 2012. Sweden.

(Continued)

Primary Examiner — Shervin Nakhjavan
(74) Attorney, Agent, or Firm — Ahab S. Ayoub (57) ABSTRACT

A method for identifying and analyzing amounts and nutritional values of food consumption, utilizing digital image processing and linked nutritional information. A recipe generator is utilized to provide a component analysis of food preparations based on identification of subcomponents.

4 Claims, 10 Drawing Sheets

(56) References Cited

OTHER PUBLICATIONS

Ovaskainen, M.L. Accuracy in the estimation of food servings against the portions in food photographs. Images. European Journal of Clinical Nutrition [Eur J Clin Nutr] May 2008; vol. 62 (5), pp. 674-681. Date of Electronic Publication: Apr. 18, 2007. E.U.

Foster, E. Accuracy of estimates of food portion size using food photographs—the importance of using age-appropriate tools. Public Health Nutrition [Public Health Nutr] Jun. 2006; vol. 9 (4), pp. 509-514. E.U.

Rollo, M.E. Trial of a mobile phone method for recording dietary intake in adults with type 2 diabetes: evaluation and implications for future applications. Journal of Telemedicine and Telecare [J Telemed Telecare] 2011; vol. 17 (6), pp. 318-323. Date of Electronic Publication: Aug. 15, 2011. Australia.

Foster, E. Developing an interactive portion size assessment system (IPSAS) for use with children. Journal of Human Nutrition and Dietetics: The Official Journal of the British Dietetic Association [J Hum Nutr Diet] Jan. 2014; vol. 27 Suppl 1, pp. 18-25. Date of Electronic Publication: May 19, 2013. U.K.

Elinder, L. Validation of personal digital photography to assess dietary quality among people with intellectual disabilities. Journal of Intellectual Disability Research: JIDR [J Intellect Disabil Res] Feb. 2012; vol. 56 (2), pp. 221-226. Date of Electronic Publication: Aug. 1, 2011. Sweden.

Brito, A. Evaluation of photographs supporting an FFQ developed for adolescents. Public Health Nutrition [Public Health Nutr] Jan. 2014; vol. 17 (1), pp. 139-144. Date of Electronic Publication: Nov. 20, 2012. Brazil.

Turconi, G. An evaluation of a colour food photography atlas as a tool for quantifying food portion size in epidemiological dietary surveys. European Journal of Clinical Nutrition [Eur J Clin Nutr] Aug. 2005; vol. 59 (8), pp. 923-931. E.U.

Subar, A. Assessment of the accuracy of portion size reports using computer-based food photographs aids in the development of an automated self-administered 24-hour recall. Journal of the American Dietetic Association [J Am Diet Assoc] Jan. 2010; vol. 110 (1), pp. 55-64. USA.

Martin, C. Measuring food intake with digital photography. Journal of Human Nutrition and Dietetics 27 (Suppl. 1) 72-81) 2014. UK.

Higgins, J. Validation of photographic food records in children: are pictures really worth a thousand words? European Journal of Clinical Nutrition [Eur J Clin Nutr] Aug. 2009; vol. 63 (8), pp. 1025-1033. Date of Electronic Publication: Mar. 4, 2009. E.U.

Chen, N. Toward Dietary Assessment via Mobile Phone Video Cameras. AMIA Symposium Proceedings, pp. 106-110. 2010 US.

* cited by examiner

FIG. 1

| RECIPE | NUTRIENT CONTENT | QC CHECK | PRINT/UPLOAD |

| DFIA NUMBER | DFIA DESCRIPTION | | | AMOUNT | UNIT | WEIGHT GRAMS | PER100GRAMRATIO |
|---|---|---|---|---|---|---|---|
| INGREDIENTS 1 | NDS NUMBER | MANUFACTURER | | AMOUNT | UNIT | WEIGHT GRAMS | PER100GRAMRATIO |
| | 0 | | | 0 | | 0 | 0 |
| INGREDIENTS 2 | NDS NUMBER 2 | MANUFACTURER 2 | | AMOUNT 2 | UNIT 2 CUP | WEIGHT GRAMS 2 | PER100GRAMRATIO 2 |
| | 0 | | | 0 | | 0 | 0 |
| INGREDIENTS 3 | NDS NUMBER 3 | MANUFACTURER 3 | | AMOUNT 3 | UNIT 3 CUP | WEIGHT GRAMS 3 | PER100GRAMRATIO 3 |
| | 0 | | | 0 | | 0 | 0 |
| INGREDIENTS 4 | NDS NUMBER 4 | MANUFACTURER 4 | | AMOUNT 4 | UNIT 4 CUP | WEIGHT GRAMS 4 | PER100GRAMRATIO 4 |
| | 0 | | | 0 | | 0 | 0 |
| INGREDIENTS 5 | NDS NUMBER 5 | MANUFACTURER 5 | | AMOUNT 5 | UNIT 5 CUP | WEIGHT GRAMS 5 | PER100GRAMRATIO 5 |
| | 0 | | | 0 | | 0 | 0 |
| INGREDIENTS 6 | NDS NUMBER 6 | MANUFACTURER 6 | | AMOUNT 6 | UNIT 6 CUP | WEIGHT GRAMS 6 | PER100GRAMRATIO 6 |
| | 0 | | | 0 | | 0 | 0 |
| INGREDIENTS 7 | NDS NUMBER 7 | MANUFACTURER 7 | | AMOUNT 7 | UNIT 7 | WEIGHT GRAMS 7 | PER100GRAMRATIO 7 |

DIGITAL FOOD IMAGING ANALYSIS: SYSTEM AND METHOD TO ANALYZE FOOD CONSUMPTION

STATEMENT REGARDING FEDERALLY SPONSORED RESEARCH OR DEVELOPMENT

The Digital Food Imaging Analysis (DFIA) invention was made with government support under Grant No. 2011-67001-30071 awarded by The United States Department of Agriculture (USDA). The government has certain rights in the invention.

BACKGROUND OF INVENTION

1. Field of the Invention

The Digital Food Imaging Analysis (DFIA) invention relates to the identification and analysis of food consumed.

2. Background Art

Because obesity and chronic disease such as diabetes and cardiovascular disease are strongly related to the amount and quality of food consumed, a need exists to improve accuracy of dietary intake and tools to assess efficacy of health programs aimed at modifying health behaviors to improve population health.

SUMMARY OF INVENTION

The technology proposed to improve accuracy, time, and cost of collecting and analyzing dietary information is the Digital Food Imaging Analysis (DFIA). The development of DFIA technology was funded by the United States Department of Agriculture (USDA) under the National Institute of Food and Agriculture award number 2011: 67001-30071. DFIA uses digital photography to identify food; new coding system (DFIA number) of food items to elaborate on how food is cooked, prepared, processed, spiced and served; software to enter, code (DFIA number) and approximate new recipes and ingredients not found in the USDA National Nutrient Database for Standard Reference (NDB SR) to food items that are found in the NDB SR; before and after meal photographs to measure consumption; software and database to determine the amount of nutrient consumed by linking DFIA number of food in photographs to food in the NDB SR. The DFIA is an expeditious and inexpensive method of quantifying value and amount of food consumed that might improve population-based surveillance of dietary intake and evaluation of health programs implementation.

Other aspects and advantages of the invention will be apparent from the following description and the appended claims.

DETAILED DESCRIPTION

Embodiments of the technology use digital photography, image processing software, food volume to weight conversion database, and the USDA National Nutrient Database for Standard Reference (NDB SR) to identify and quantify the value of food consumption. Photographs of meals taken before and after are used to calculate amounts consumed. It was originally designed to measure the nutritional value of food served to students in school cafeterias. But more recently this technology is being translated to primary care physician offices for self-assessment and management of dietary intake in the treatment of obesity and management of weight. The DFIA is an expeditious and inexpensive method of quantifying value and amount of food consumed. This information might improve population-based surveillance of dietary intake, evaluation of health program implementation, and prevention of chronic disease.

Figure 1:
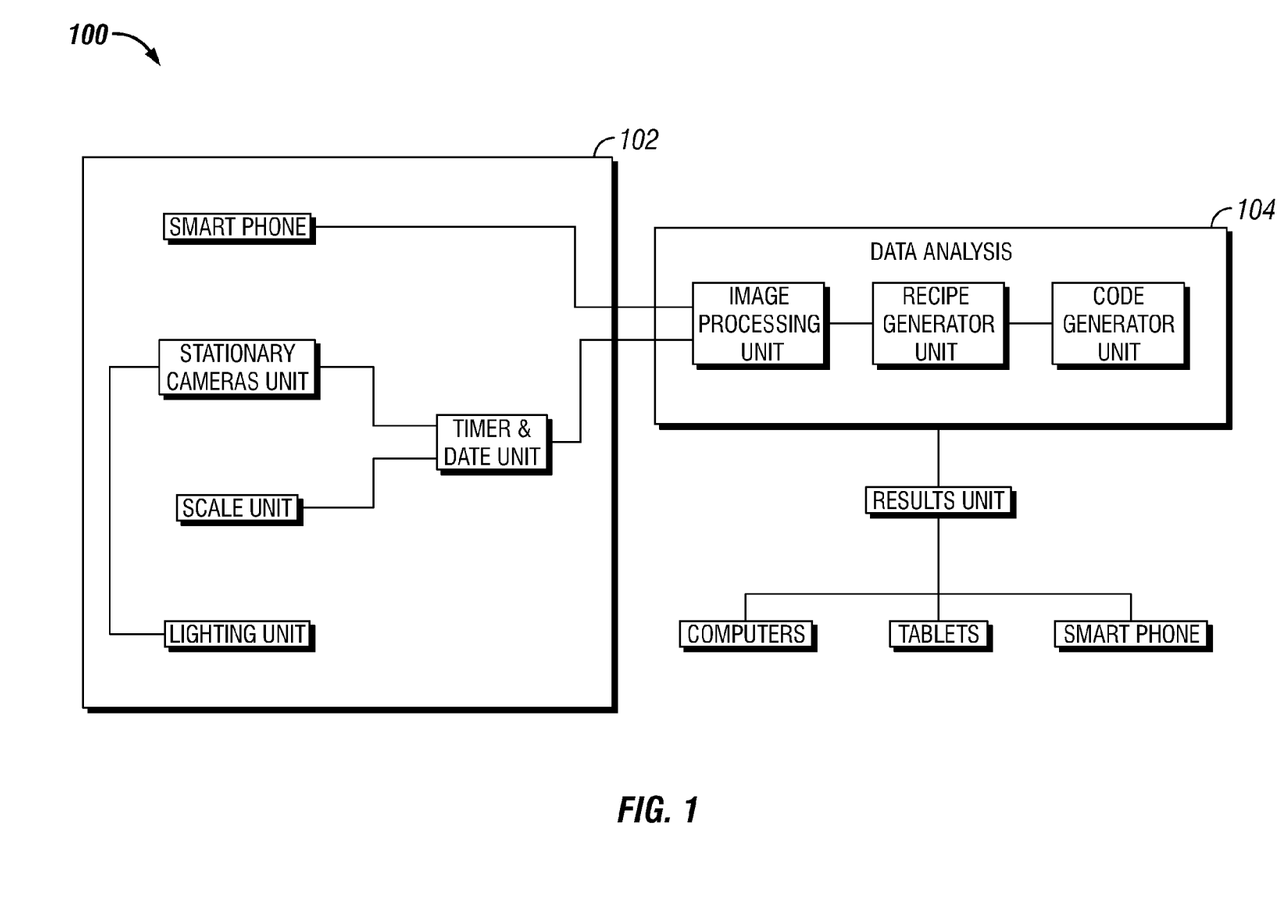
FIG. 1 shows the diagram for the DFIA instrument.

As shown in FIG. 1, an embodiment of the DFIA system typically includes an Image Collection system operatively connected to a Data Analysis system, configured to provide results to a user via, e.g., various electronic devices. As will be further described in detail, the data collection occurring via the Image Collection system may include digital images captured via one or more cameras, weights collected via a scale, and a lighting component such as a flash for use with image capture, and will typically be configured to associate a time and date with the image and data capture. In one embodiment, a smart phone having communications and image capture capability may be utilized as the Image Collection system.

One embodiment of the DFIA method includes creation of a DFIA number for each food item (approximately 9000), in the NDB SR (currently release 27). The DFIA number provides a granular description of each food item which NDB SR lacks. The NDB SR is a 5-digit number and the DFIA number an 11-14 digit number that uniquely identify food items. With the NDB SR the first 2 digits relate to the food group and the following 3 digits are used to enumerate foods in that group and some preparation descriptions. Each food item in the NDB SR has a long description containing the name of the food with relevant characteristics, e.g., raw or cooked, enriched, color.

To create the DFIA number a computer algorithm was developed at the Social and Health Research Center (SAHRC). The code describes the food item (e.g. corn), food group (e.g. vegetable), brand/type (e.g. Del Monte), processing/packaging (e.g. canned), pre-preparation (e.g. with/without cream), preparation (e.g. mashed), cooking type (e.g. baked), cooked with (e.g. butter), grade/spices (e.g. pepper), and served with (e.g. butter). Each of these descriptions provides a numerical value. A DFIA number consists of 11-14 digits. Near 9000 food items from NDB SR were catalogued at SAHRC with an associated unique DFIA number.

Figure 2:
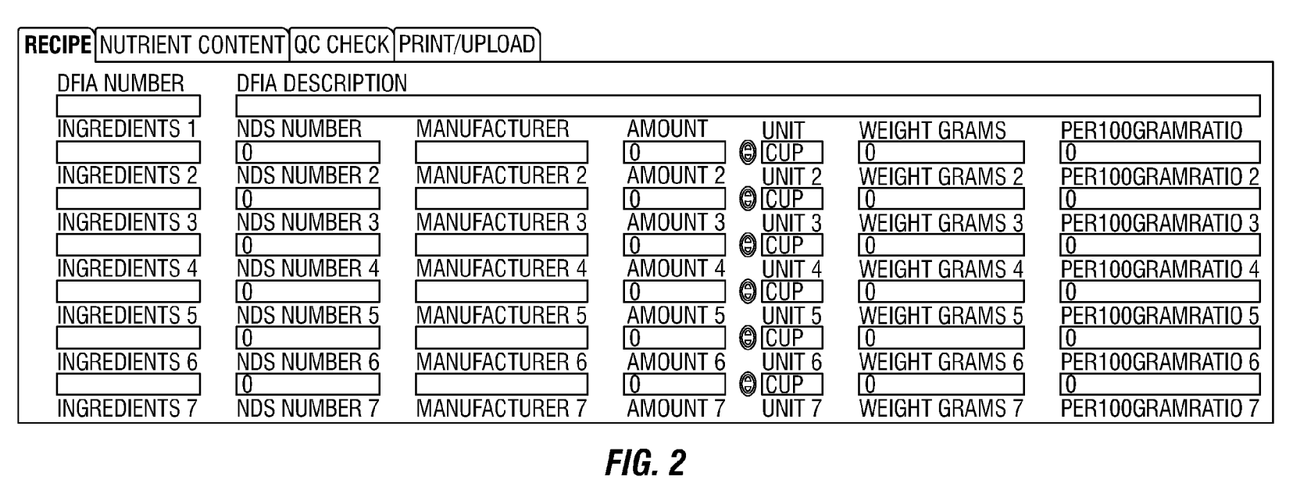
FIG. 2 shows the Recipe Generator Main Window

One embodiment comprises a Recipe Generator. Many school district food services, local restaurants and home cooked food items are not included in the NDB SR, such as green enchiladas, chicken mole or caldo de pollo. SAHRC analysis expands upon the NDB SR by adding local and homemade foods. Production records, recipes and ingredients for these food items were collected from school food service departments, restaurants, and parents. A DFIA number was assigned to each food item using the previously-described methods to expand upon NDB SR, by incorporating recipes and ingredients. In order to determine the nutritional value of the new food item (e.g., recipe), its ingredients needed to approximate ingredients of the NDB SR. To automate this operation, the Recipe Generator software was designed at SAHRC. FIG. 2 shows a screenshot of the Recipe Generator main window, showing customized linkages including: (a) NDB number specific for the USDA's NDB SR database, (b) html path to manufacturer's UPC Codes, (c) array of restaurant foods, and (d) listings of commercial food items.

Figure 3:
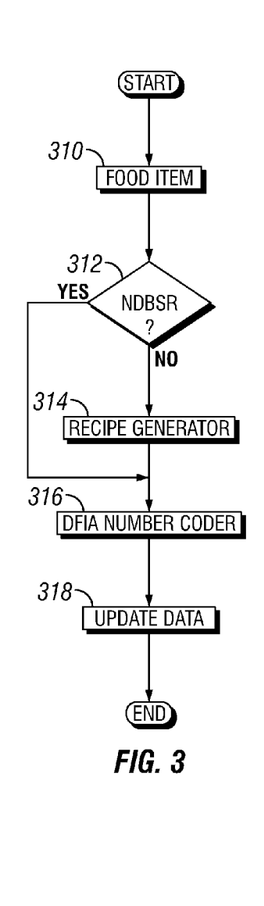
FIG. 3 shows the Recipe Generator algorithm diagram

One embodiment of a method to incorporate a new food item into the DFIA system via the Receipt Generator is shown in FIG. 3. A food item is provided 310 and the NDBSR is searched for that food item 312. If the food item is not found in the NDBSR, it is submitted to the recipe generator 314 for analysis. Once the contents of the food item are identified, a DFIA number is assigned to the food item 316, and the database is updated 318.

Referring to FIGS. 2-3 and using a school menu chicken nugget salad by way of example, the process according to one embodiment of the DFIA system is as follows: 1) the production records with ingredients and serving size amounts in grams of the chicken nugget salad are obtained from the school food service department; 2) the new DFIA number for chicken nugget salad created at SAHRC is entered in the "DFIA Number" space at the top left; 3) an accurate and specific DFIA description for the new food item is then entered to the right within the "DFIA Description" space; 4) each ingredient—chicken nuggets, lettuce, cucumber, and cherry tomato including their weight in grams—is entered in an associated field of the Recipe Tab; 5) the four ingredients are searched in the most current NDB SR until an NDB number is identified that most closely matches, both descriptively and nutritionally, to those from the school production records. Once identified, the NDB number is incorporated and associated with the respective ingredient within the "NDB Number" space; 6) upon initial execution of the Recipe Generator by a user (via e.g., clicking of a prompt), all ingredients are standardized to a predetermined weight, typically 100 g to match NDB SR units. The reason for food weight conversion is that the basic unit of measure in NDB SR nutrient composition is defaulted to 100 grams. For example, 284 g of chicken nugget salad consist of 134 g of nuggets, 72 g of lettuce, 27 g of cucumber, and 51 g of cherry tomato. Of these, for a 100 g ratio the values are 47% nugget, 25% lettuce, 10% cucumber, and 18% cherry tomato; 7) within the Nutrient Content Tab, NDB SR is read and when further initiated by a user (via e.g., clicking of a prompt) provides the nutrients for the four ingredients from the NDB number; 8) within the QC Check Tab, the serving size in grams, energy, carbohydrate, protein, fat, sugar, sodium, calcium, and vitamin A and D of the ingredients provided from the school production record are entered; 9) when "Run" is pressed once more a comparison of the nutrients is made between the school production record and NDB SR; and either 10a) if the difference of the nutrients between the school production record and NDB SR is greater than 20% per ingredient, the NDB SR is further queried to find similar ingredients that nutritionally compare as closely as possible with the school production record; or 10b) if the difference of the nutrient values of each ingredient between the school production record and NDB SR is 20% or less, the chicken nugget salad record has passed protocol and is then incorporated into the DFIA number master database, typically hosted via an operatively-connected server.

Once all food items in the expanded SR database are catalogued with a DFIA number, they are stored in SAHRC's server that contains the DFIA library. This library now consists of 8300 food items.

Another aspect of embodiments of the DFIA method comprises the conversion of food volume to food weight in grams. The primary reason behind the conversion of food from volume to weight is that the NDB SR is defaulted at units of 100 grams. NDB SR is the principal source of nutrient composition for most if not all nutrient analysis tools, including the DFIA. Food weight conversion is very important in nutrient analysis because, proportions of food weights are typically used as a multiplier to NDB SR for retrieving nutrient composition. In dietary recalls, food volumes are estimated using memory recalls and supported by a number of visual guides (i.e. deck of cards, baseball, food pictures, and models). Conversely, other methods utilize food frequency questionnaires to estimate food volume using 3-4 predefined choices (i.e. ½, 1 and 2 cups or some, a little, and a lot). As a result, these data collection methods are susceptible to a number of measurement errors. Because of these limitations, the DFIA techniques are configured to improve or resolve errors often associated in food weight conversions. Thus, a principal analytical advantage of DFIA is the use of an image as evidence of the food that have been served (Before Picture) and consumed (After Picture).

The mathematical relationship that expresses the conversion for the total amount consumed in the DFIA is presented as follows:

$$ENC_i = DFCC_i * RNC_i(N_{ij}) \qquad \text{Equation 1}$$

Wherein, $ENC_i$ is the estimated nutrient composition per selected food item i=DFIA Code; $DFCC_i$ is the Digital Food Consumption Coefficient for the same selected food item i; and $RNC_i$ is the Real Nutrient Composition for the food item i as a function of the corresponding macro and micro nutrient values $N_{ij}$ where j=1 . . . m and m=amount of nutrients for each i=DFIA Code (i.e. kcal, vitamins, minerals, proteins, amino acids, sugars, fatty acids and more). DFCC is the proportion of food weights in grams.

Figure 4:
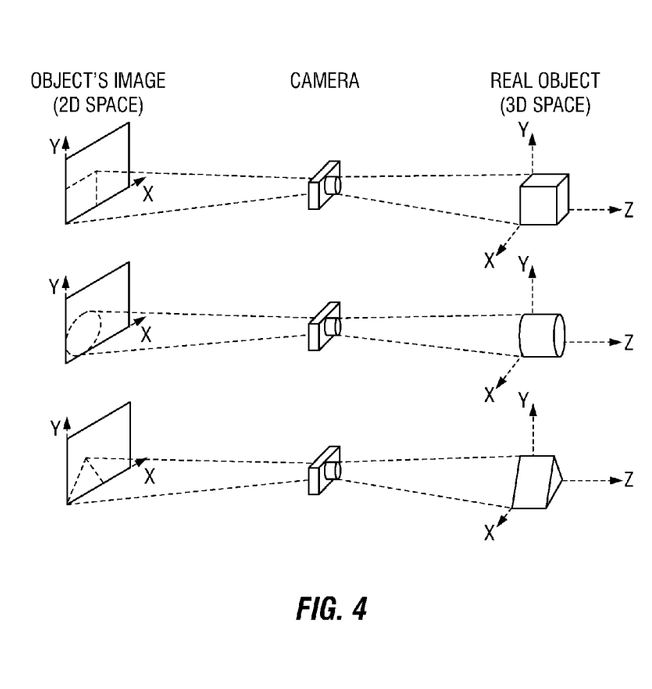
FIG. 4 shows geometric and image relationship used to calculate the DFCC.

As shown in FIG. 4, image processing according to one embodiment of the DFIA translates a three dimensional object (food item) into a two dimensional image of the same object. The volume of the real object is directly associated with the area of the image in the picture. The volume is also associated with a weight for each food item, based on its density. DFIA considers the variation in textures, densities, colors and shapes for each food item. This variation is captured by the picture in which the image could be affected by the variation and consequently it impacts the results in the estimation of the area.

The preliminary knowledge of the volume and weight of the food item facilitates the association with the image area. For those food items that only is known their volume, the DFIA database includes the density for the 8,194 food items listed in the NDB SR.

Figure 5:
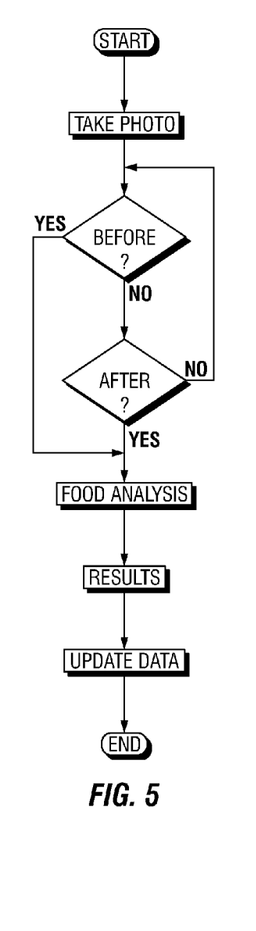
FIG. 5 shows the flow diagram for the DFIA software.
Figure 6:
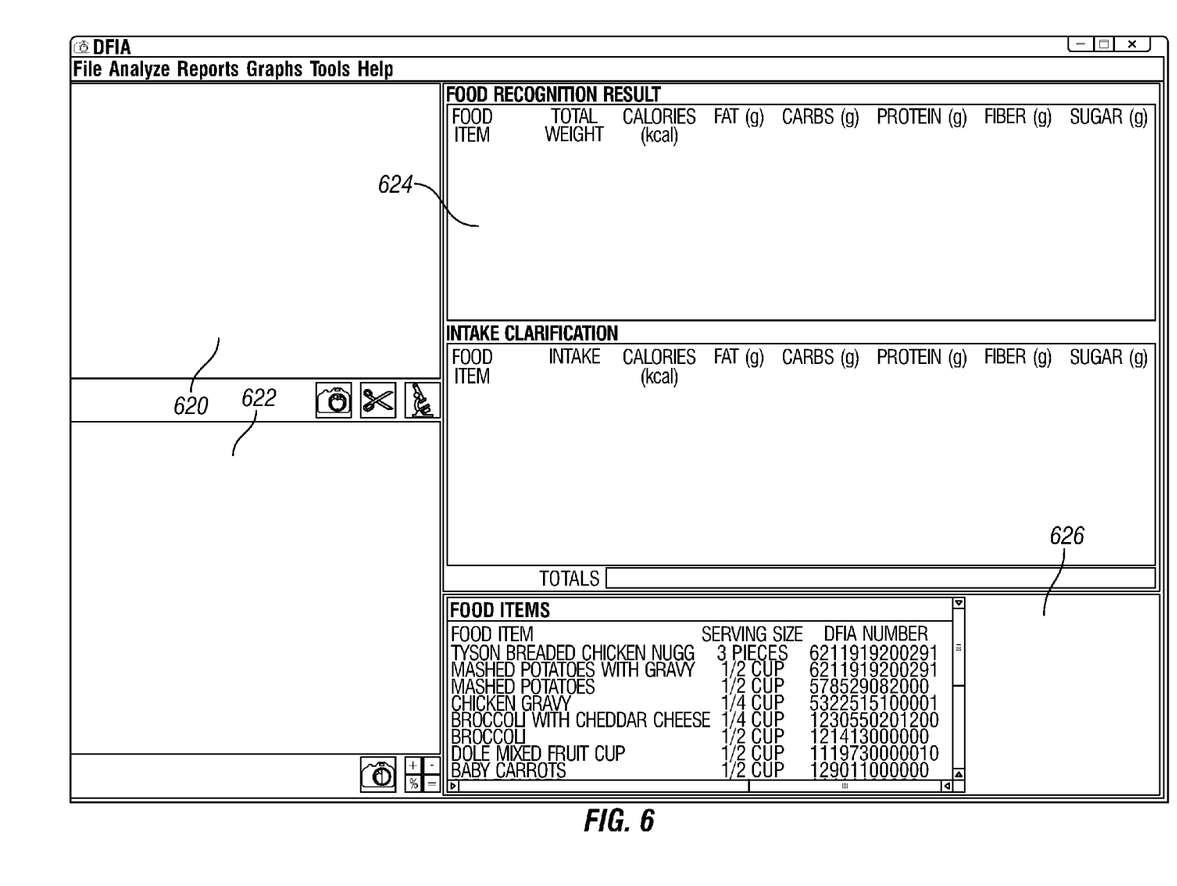
FIG. 6 shows the main DFIA window.

The analysis and estimation of the area for the food item image in the digital picture incorporates the following aspects: edge detector, noise reduction system, and image threshold capability. FIG. 5 is a flow diagram of the general process of evaluating food from an image according to one embodiment. Once a photo is taken, it is identified as being either a before or after image, and then analysis continues, as further described herein.

By using the appropriated mathematical operators each pixel is individually analyzed in order to determine which one truly belongs to the image of the food item and excluding those pixels belonging to the background. The total of the pixels belonging to the food item image represents the area on the image.

The precision of the DFIA instrument is based on the ability of efficiently determining the area of the food item image. The software's algorithm is designed to accurately differentiate the pixels belonging to the food image from the background and estimating the area.

In the embodiment of DFIA technology determining the error associated with the variation on area of the image for the same food item. Due to the way the food item is served on the tray a variation in the area in the pictures is observed. The variation is determined by taking a series of images of the same food item served by different personal and calculating the standard deviation of the area for each image.

$$SDOA = 1/n \Sigma_{i=1}^{n}(BA-\overline{BA})^2 \qquad \text{Equation 2}$$

Where, SDOA is the Standard Deviation of the Area, BA is the Before Area from the before image, and $\overline{BA}$ is the mean of the before area from the n samples taken. The calculated SDOA is considered while reporting the Digital Food Consumption Coefficient.

The embodiment of DFIA instrument defines the Digital Food Consumption Coefficient (DFCC) as the modifier that quantifies the consumption values for volume, weight, calories and nutrients of each food item. The equation 3 describes the relationship between the DFCC and the areas of the images from the before and after pictures.

$$DFCC_i = BA_i - AA_i/BA_i \qquad \text{Equation 3}$$

Where i=DFIA code, $BA_i$ is the area of the image for the before picture, and $AA_i$ is the area for the image of the after picture.

Approximately 400 of the foods more commonly served at school cafeterias were photographed for establishing the association between the area of their images and the corresponding volume and weighed at 100% of a standard servings, and then archived in the DFIA database. These referential image parameters and food weights are multiplied by the matching DFCC and the results are the final consumption values.

The software's features, windows and the icons are shown in FIGS. 6-12. Referring to the screenshot of the embodiment of FIG. 6, the DFIA main window is subdivided into sections and in this example, the upper and lower sections on the left side are reserved for pre-consumption 620 and post-consumption 622 images of food (images not shown in FIG. 6). The upper right section is the Food Recognition section 624 for display of recognized food components, based on the images to be loaded into 620 and 622. The lower right section 626 lists the food item candidates identified from supplied data regarding a menu or food inventory. Utilizing a list of food item candidates advantageously narrows the universe of potential food candidates, thereby increasing the accuracy of food identification based on images captured by the system.

Figure 7:
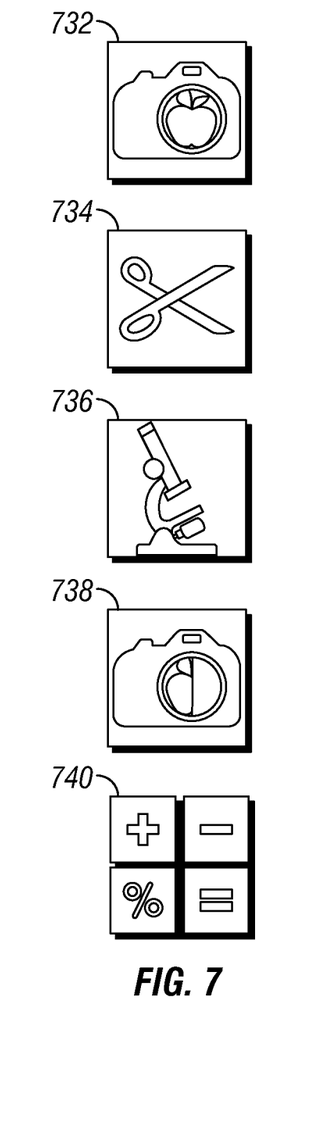
FIG. 7 shows the DFIA main window icons.

FIG. 7 shows one embodiment of representative user-selectable icons used by the DFIA system. Generally, these include icons to load captured images 732, 738, to select the tray type 734, to identify and analyze the identified foods 736, and to calculate food/nutrient intake amounts 740.

Figure 8:
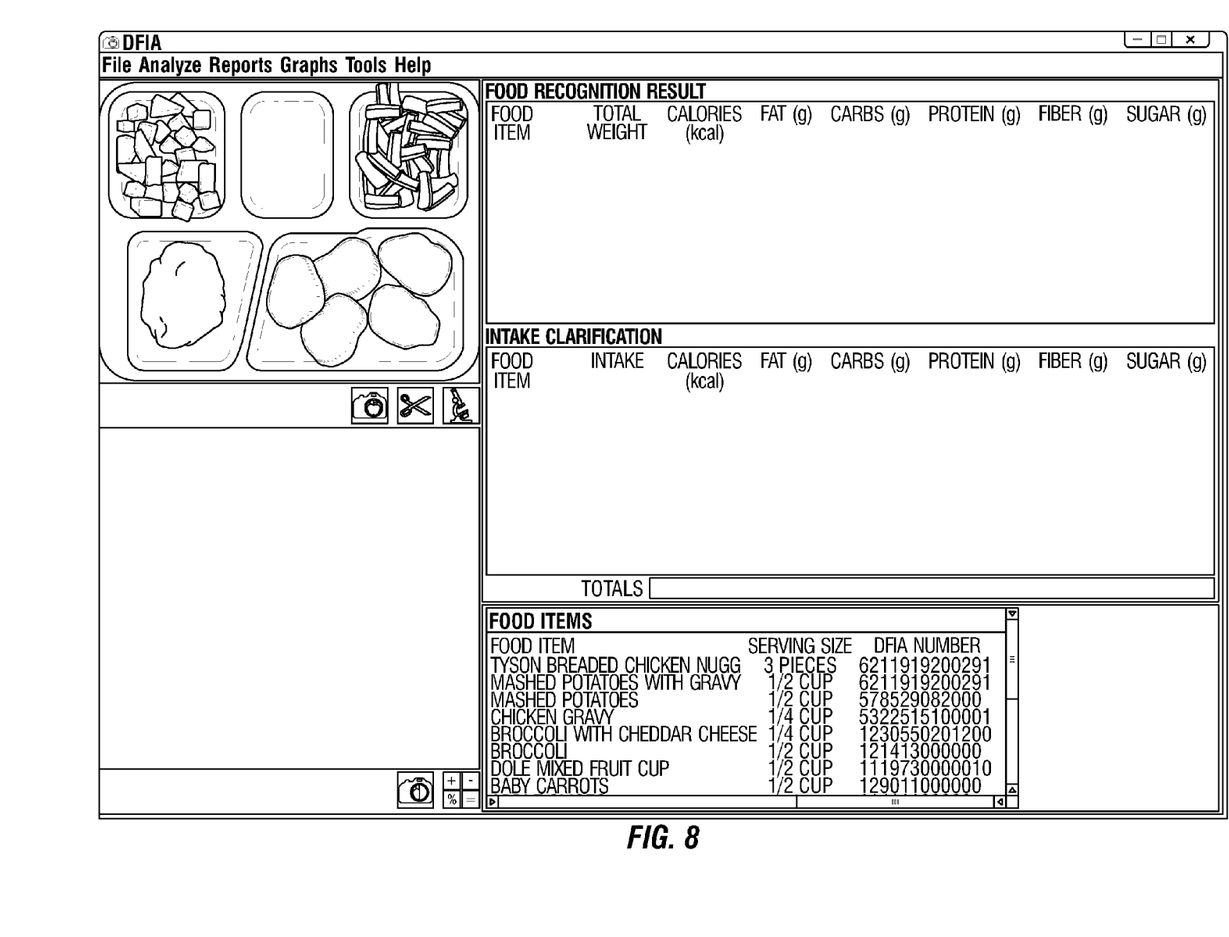
FIG. 8 shows a pre-consumption photo of an uploaded meal in the DFIA software.

In the screenshot of FIG. 8, the before meal photo image is displayed in the upper left window, while the after meal photo would be displayed in the lower left window. An ID number associates an individual with the before and after meals. This ID is then entered and recorded by the system.

Figure 9:
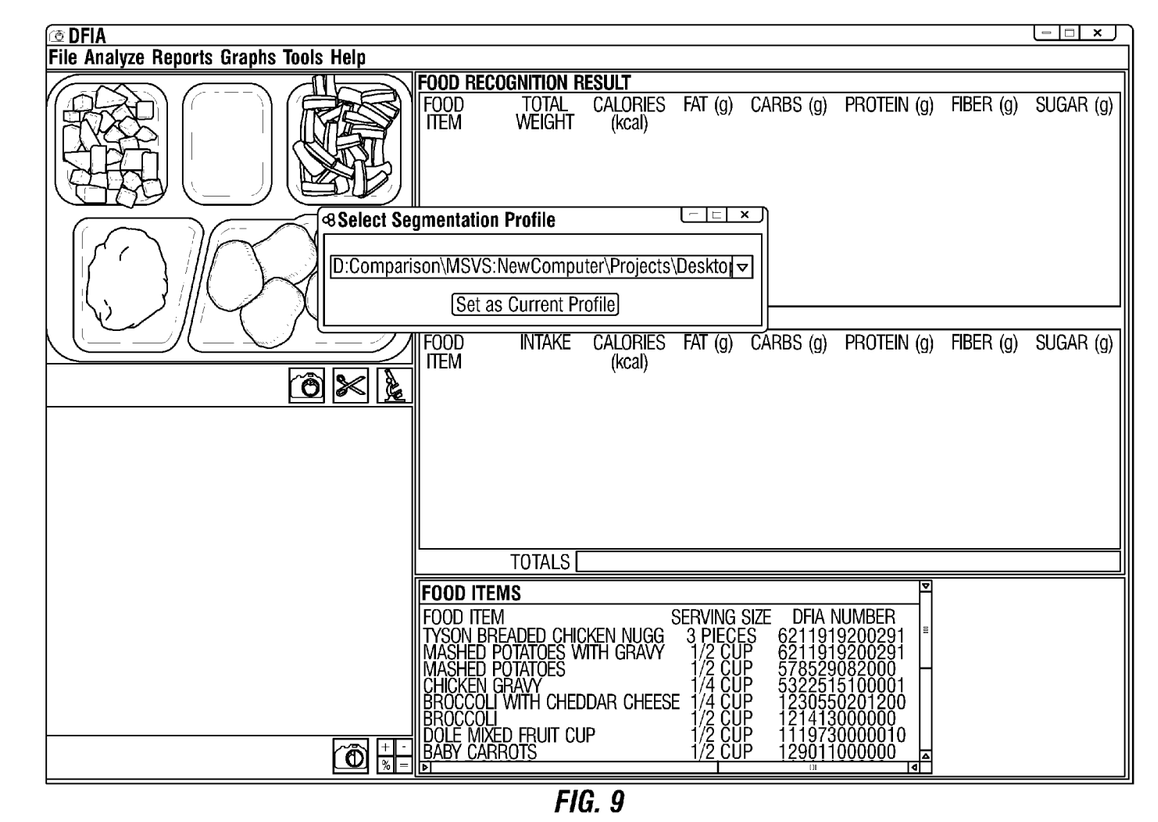
FIG. 9 shows a food tray type identifier feature of the DFIA software.

As shown in the screenshot of FIG. 9, a prompt requests identification of the tray. Because multiple tray sizes and configurations are possible, by choosing the tray type, the correct coordinates and segmentations for each compartment on the tray will be identified and loaded.

Figure 10:
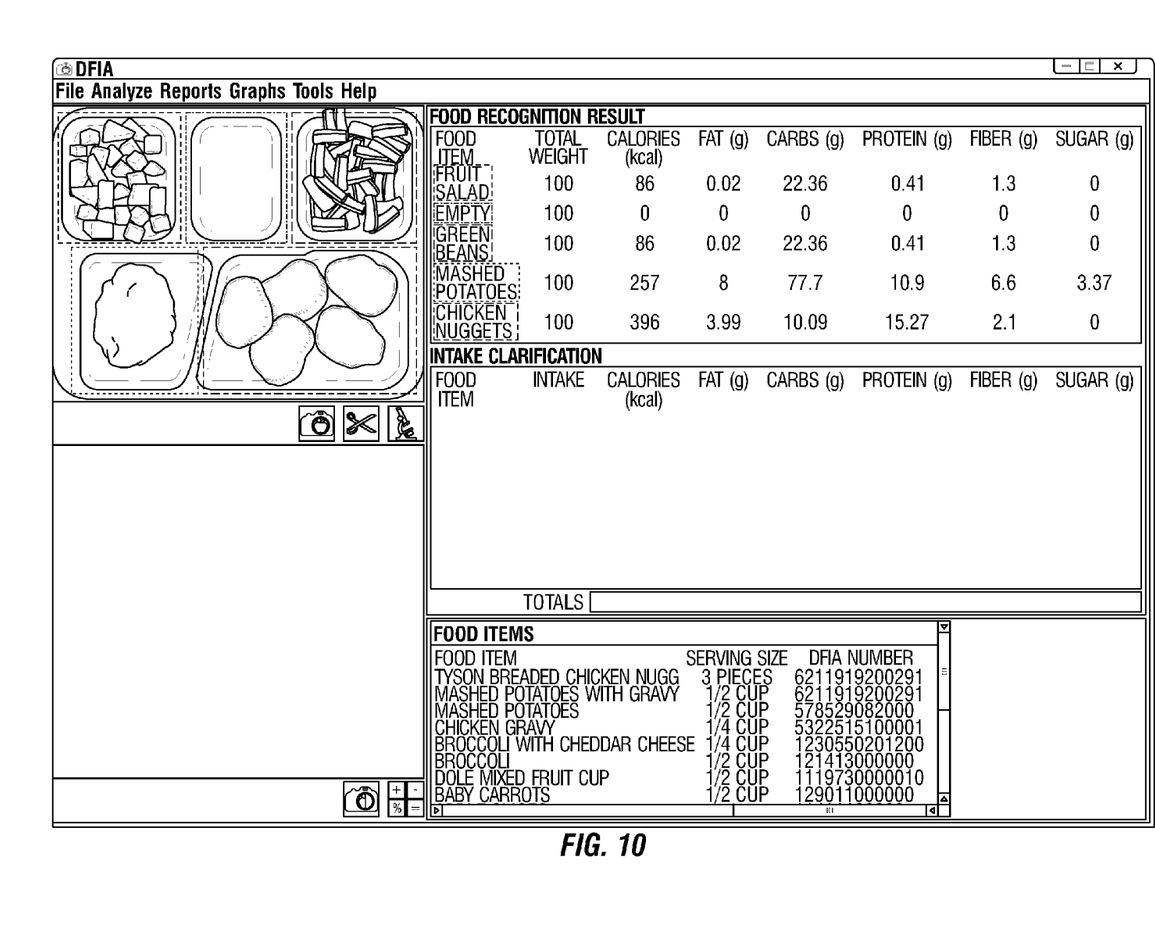
FIG. 10 shows the food recognition window of the DFIA software.
Figure 11:
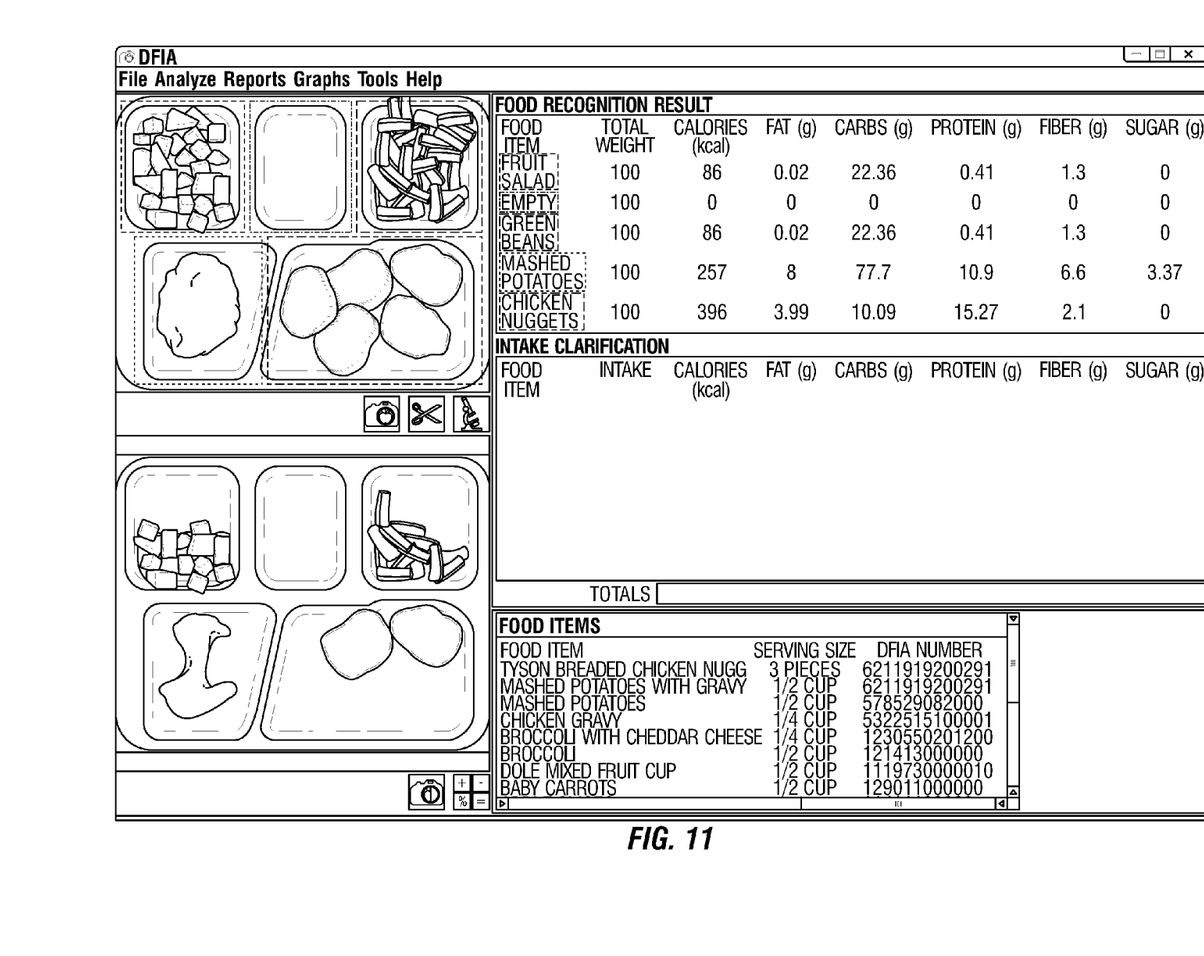
FIG. 11 shows pre- and post-consumption photos of meals with nutrient analysis results in the food recognition window of the DFIA software.

The food is identified by tray compartment and the foods then are listed in the Food Recognition window. A specific color or other identifier may be assigned to each tray compartment and the same color/identifier may be used in the Food Recognition window as shown in FIG. 10 to identify the contents of each compartment. At this point the before meal photo image is linked with the DFIA nutrient database retrieving the nutritional values. When the identification process is finished and results displayed in the Food Recognition window, the after meal photo image is uploaded as shown in FIG. 11.

Figure 12:
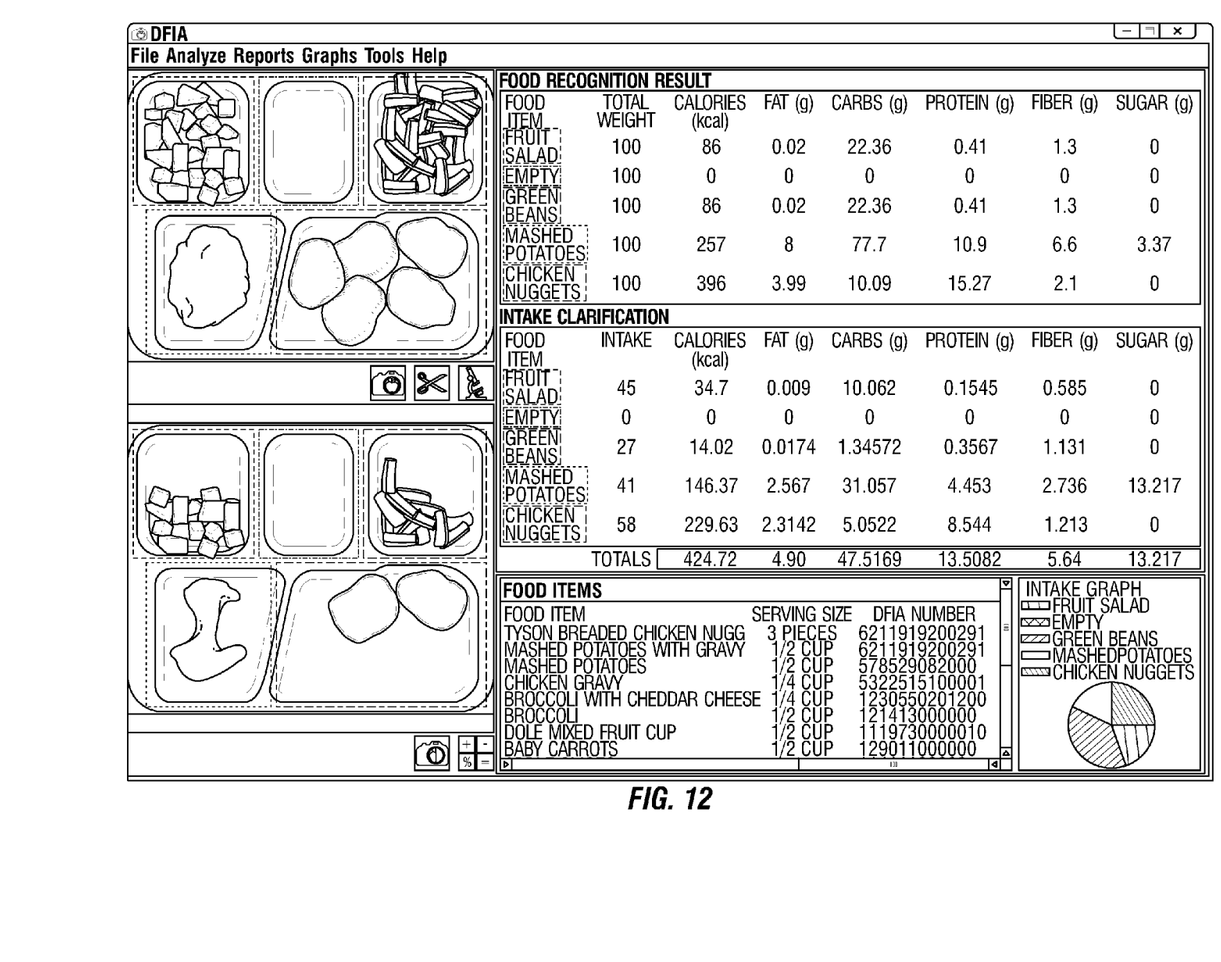
FIG. 12 shows nutrient analysis chart of food consumed, in the intake quantification window of the DFIA software.

From the after meal picture the DFIA software computes the amount of food consumed (before meal values—after meal values=consumption). The nutritional values for consumption are calculated from the values derived from the database with DFIA—NDB SR linkage. These values are listed in the Intake Quantification window as shown in FIG. 12. In addition, interpretation of results, charts and other tools to customize a report have been added to the software.

Advantages of the DFIA technology include the capability of real-time monitoring of consumption and consumer data, as well as consumer activity in a food service setting and other health environments such as primary care physician offices. Many school system food programs receive federal aid funds, and are expected to meet certain mandated criteria. Real-time monitoring may be desirable in such systems, to permit real-time (or delayed, streaming) viewing of the efficiency and activity of such systems.

In the school cafeterias the DFIA system includes two stationary cameras: one camera oriented to capture a food serving area usually near the cash register and second camera near the disposal window to capture food waste. As a student passes by the cash register with a food tray he/she shows a placard with the name and ID (pictures of students are not taken) where a photograph is snapped of the food tray. The taking of digital photographs is minimally intrusive and expeditious. The student placard ID and the camera recording of time links students to dietary patterns during a time period in the day. Such a system advantageously associates a particular meal with its consumer. For example, in a children's cafeteria setting, it may be desirable to avoid capturing personally identifying information relating to individual children, while still maintaining the ability to associate a child (or an ID associated with a child) to food consumption. Thus, a system that captures an assigned ID (consumer identifier) such as a bar/QR code, with the food image, will advantageously provide the capability to maintain privacy while still associating the consumption data with the child.

A benefit to school food service managers is the measure of food wasted. Non-consumption data can be assessed as well to determine amount and type of food wasted. Which types of foods are less likely to be consumed is useful information, in order to better direct future nutritional purchase and planning for the managers. It may also be useful in assessing a student's overall dietary patterns by understanding which deficiencies may be arising due to their decreased consumption.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A non-transitory computer readable storage medium comprising software instructions that, when executed by a processor, cause the processor to:
   compare an acquired digital image of food to at least one stored digital image to determine whether the food in the acquired digital image matches the food in the at least one stored digital image based on predetermined accuracy criteria;
   associate the acquired digital image of food with at least one selected from (a) a DFIA number and (b) an NDB SR number, associated with the food from the stored digital image, if the predetermined accuracy criteria is met; and
   associate nutritional information with the food in the acquired digital image, the nutritional information being that associated with the at least one selected from the DFIA number and the NDB SR number.

2. The non-transitory computer readable storage medium of claim 1, wherein the software instructions, when executed by the processor, also cause the processor to calculate a food volume comparison between the acquired digital image and a second acquired digital image, wherein the acquired digital images are both associated with the consumption of a particular meal.

3. The non-transitory computer readable storage medium of claim 2, wherein the software instructions, when executed by the processor, also cause the processor to combine the nutritional information with the volume comparison to calculate a nutritional consumption analysis of the particular meal.

4. The non-transitory computer readable storage medium of claim 1, wherein the software instructions, when executed by the processor, also cause the processor to contact a remote networked database, the database comprising at least one selected from the DFIA number and the NDB SR number.

* * * * *